US005863984A

United States Patent [19]
Doillon et al.

[11] Patent Number: 5,863,984
[45] Date of Patent: Jan. 26, 1999

[54] BIOSTABLE POROUS MATERIAL COMPRISING COMPOSITE BIOPOLYMERS

[75] Inventors: Charles J. Doillon, Montchatel, Canada; Krystina Pietrucha, Lodz, Poland; René C. Gaudreault, Berniéres, Canada

[73] Assignee: Université Laval, Cité Universitaire, Quebec, Canada

[21] Appl. No.: 566,297

[22] Filed: Dec. 1, 1995

[51] Int. Cl.$^6$ ............................... C08L 89/00; A61F 2/00
[52] U.S. Cl. ........................ 525/54.1; 523/113; 424/423; 424/426; 424/484
[58] Field of Search .......................... 525/54.1; 523/113; 424/426, 423, 484

[56] References Cited

U.S. PATENT DOCUMENTS

| | | | |
|---|---|---|---|
| 4,101,380 | 7/1978 | Rubinstein et al. | 195/63 |
| 4,179,337 | 12/1979 | Davis et al. | 435/181 |
| 4,840,851 | 6/1989 | Golander et al. | 428/523 |
| 4,871,490 | 10/1989 | Rosiak et al. | 264/22 |
| 4,904,708 | 2/1990 | Kaetsu et al. | 522/5 |
| 4,970,298 | 11/1990 | Silver et al. | 530/356 |
| 5,162,430 | 11/1992 | Rhee et al. | 525/54.1 |
| 5,290,548 | 3/1994 | Goldberg et al. | 424/78.18 |

FOREIGN PATENT DOCUMENTS

| | | |
|---|---|---|
| 0 568 334 A1 | 11/1993 | European Pat. Off. . |
| 93/13753 | 7/1993 | WIPO . |

OTHER PUBLICATIONS

Doillon et al, "Porosity and biological properties of polyethylene glycol–conjugated collagen materials," *Journal of Biomaterials Science*, Polymer Edition, vol. 6, No. 8, pp. 715–728, 1994.
A. Abuchowski, et al., "Alteration of Immunological Properties of Bovine Serum Albumin by Covalent Attachmant of Polyethylene Glycol", *J. Biol. Chem.*, 252, 3578–3581, (Jun. 1977).
T. M. Allen, et al., "Liposomes Containing Synthetic Lipid Derivatives of Poly(ethylene glycol) Show Prolonged Circulation Half–Lives in Vivo", *Biochem. Biophys. Acta*, 1066, 29–36, (1991).
S. Amudeswari, et al., "Short–Term Biocompatibility Studies of Hydrogel–Grafted Collagen Copolymers", *J. Biomedical Materials Research*, 20,1103–1109, (1986).
A. Apicella, et al., "Poly(ethylene oxide) (PEO) and Different Molecular Weight PEO Blends Monolithic Devices for Drug Release", *Biomaterials*, 14, 83–90, (1993).
G. Blume, et al., "Specific Targeting with Poly(ethylene Glycol)–Modified Liposomes: Coupling of Homing Devices to the Ends of the Polymeric Chains Combines Effective Target Binding with Long Circulation Times", *Biochem. Biophys. Acta*, 1149, 180–184, (1993).
A. A. Bogdanov, et al., "A New Macromolecule as a Contrast Agent for MR Angiopraphy: Preparation, Properties, and Animal Studies", *Radiology*, 187, 701–706, (1993).

M. Carenza, "Recent Achievements in the Use of Radiation Polymerization and Grafting for Biomedical Applications", *Radiat. Phys. Chem.*, 39, 485–493. (1992).
H. C. Chiu, et al., "Enzymatic Activity of Chymotrypsin and Its Poly(ethylene glycol) Conjugates Toward Low and High Molecular Weight Substrates", *Bioconjugate Chem.*, 4, 290–295, (1993).
M. Chvapil, et al., "Some Chemical and Biological Characteristics of a New Collegen–Polymer Compound Material", *J. Biomed. Materials Research*, 3, 315–332, (1969).
L. Civerchia–Perez, et al., "Use of Collegen–Hydroxyethylmethacrylate Hydrogels for Cell Growth", *Proc. Natl. Acad. Sci., USA*, 77, 2064–2068, (Apr. 1980).
P. H. Corkhill, et al., "Synthetic Hydrogels VI. Hydrogel Composites as Wound Dressings and Implant Materials", *Biomaterials*, 10, 3–10, (Jan., 1989).
M. F. Côté, et al., "In Vitro Contraction Rate of Collagen in Sponge–Shape Matrices", *J. Biomaterials Sci. Polymer Edn*, 3, 301–313, (1992).
M. F. Côté, et al., "Wettability of Cross–Linked Collagenous Biomaterials: In Vitro Study", *Biomaterials*, 13, 612–616, (1992).
C. Delgado, et al., "The Uses and Properties of PEG–Linked Proteins", *Crit. Reviews Therapeutic Drug Carrier Systems*, 9, 249–304, (1992).
C. J. Doillon, "Skin Replacement Using Collegen Extracted From Bovine Hide", *Clinical Materials*, 9, 189–193, (1992).
L. G. Garkavenko, et al., "Modification of Macroporous Silica Gel with Polyethylene Glycol by Exposure to Radiation", *Kolloidn. Lh.*, 48, 534–536, (1986).

(List continued on next page.)

*Primary Examiner*—Nathan M. Nutter
*Attorney, Agent, or Firm*—Schwegman, Lundberg, Woessner & Kluth, P.A.

[57] ABSTRACT

Biomaterials like collagen can be designed for use as scaffolds for connective tissue reconstruction. It is known that proteins conjugated with PEGs exhibit a decrease in their biodegradation rate and their immunogenicity. Different concentrations and molecular weights of PEGs (PEG-750 and PEG-5000) were conjugated by chemical or irradiation means to collagen materials (films or sponges) which were then investigated by physicochemical assays, collagenase assay, fibroblast cell culture and subcutaneous implantation. PEG-conjugation delayed the degradation by collagenase and preserved a normal fibroblasts morphology and confluency in culture. In vivo, the porous structure of non-modified sponges was collapsed by day 15 with few observable fibroblasts between the collagen fibers. In PEG-modified collagen sponges, the porous structure remained stable for at least 30 days. Cell infiltration was particularly enhanced in PEG-750-conjugated collagen sponges. In conclusion, PEGs conjugated onto collagen sponges stabilize the porous structure without deactivating the biological properties of collagen. These porous composite materials could advantageously function as a scaffold to organize tissue ingrowth. Therefore, the present invention relates to a porous biomaterial whose porosity is stabilized by conjugation to PEG-derivatives. Biopolymers other than collagen may be used in the making of such composite materials.

16 Claims, 4 Drawing Sheets

OTHER PUBLICATIONS

Y. Gotoh, et al., "Chemical Modification of Silk Fibroin with Cyanuric Chloride–Activated Poly(ethylene glycol): Analyses of Reaction Site by 1H–NMR Spectroscopy and Conformation of the Conjugates", *Bioconjugate Chem.*, 4, 554–559, (1993).

M. S. Hershfield, et al., "Treatment of Adenosine Deaminidase Deficiency with Polyethylene Glycol–Modified Adenosine Deaminase", *New England J. Med.*, 316, 589–596, (Mar. 1987).

T. Hino, et al., "Introduction," In: *Biocompatibility of Tissue Analogs*, vol. II, pp. 72–87, (1985).

H K. Kleinman, et al., "Use of Extracellular Matrix Components for Cell Culture", *Analytical Biochem.*, 166, 1–13, (1987).

A. L. Klibanov, et al., "Activity of Amphipathic Poly(ethylene glycol) 5000 to Proling the Circulation Time of Liposomes Depends on the Liposome Size and is Unfavorable for Immunoliposome Binding to Target", *Biochim. Biophys. Acta*, 1062, 142–148, (1991).

T. P. Kogan, "The Synthesis of Substituted Methoxy–Poly(ethyleneglycol) Derivatives Suitable for Selective Protein Modification", *Synthetic Commun.*, 22, 2417–2424, (1992).

S. T. Li, et al., "Design and Development of a Collagen Based Meniscus Implant for Meniscal Fibrocartilage Regeneration", Abstract, 20th Annual Meeting of the Society for Biomaterials, p. 255, (Apr., 1994).

M. J. Lydon, et al., "Cellular Interactions with Synthetic Polymer Surfaces in Culture", *Biomaterials*, 6, 396–402, (Nov. 1985).

J. Marchal, "Radiation–Induced Oxidative Degradation of Polyoxyethyleneglycol in Dilute Solutions in Chloroform and in Water", In: *Radiation Research 1996*, North–Holland Publishing Co., Amsterdam, 327–338, (1967).

E. J. Miller, et al., "Preparation and Characterization of the Different Types of Collagen", *Methods in Enzymol.*, 82, 33–64, (1982).

T. Miron, et al., "A Simplified Method for the Preparation of Succinimidyl Carbonate Polyethylene Glycol for Coupling to Proteins", *Bioconjugate Chem.*, 4, 568–569, (1993).

A. Nathan, et al., "Copolymers of Lysine and Polyethylene Glycol: A New Family of Functionalized Drug Carriers", *Bioconjugate Chem.*, 4, 54–62, (1993).

D. Needham, et al., "Repulsive Interactions and Mechanical Stability of Polymer–Grafted Lipid Membranes", *Biochim. Biophys. Acta*, 1108 40–48, (1992).

L. O. Persson, et al., "Synthesis of ATP–Polyethylene Glycol and ATP–Dextran and Their Use in the Purification of Phosphoglycerate Kinase From Spinach Chloroplasts Using Affinity Partitioning", *J. Chromatography*, 457, 183–193 (1988).

K. Pietrucha, "Effect of Irradiation of Collagen Solutions in Relation to Biomedical Applications", *Polymers in Medicine*, 19, 3–18, (1989).

K. Pietrucha, et al., "ESR Investigations of Radiation Grafting of Methyl Methacrylate in Aqueous Emulsion onto Chrome–Tanned Pig Skin", *Radiat. Phys. Chem.*, 16, 315–318, (1980).

K. Pietrucha, "New Collagen Implant as Dural Substitute", *Biomaterials*, 12, 320–323, (Apr. 1991).

K. Pietrucha, et al., "Some Reactions of OH Radicals with Collagen and Tyrosine in Aqueous Solutions", *Radiat. Phys. Chem.*, 36, 155–160, (1990).

J. K. Rao, et al., "Implantable Controlled Delivery Systems for Proteins Based on Collagen–pHEMA Hydrogels", *Biomaterials*, 15, 383–389, (1994).

W. Rhee, et al., "Bovine Collagen Modified by PEG", In: *Poly(Ethylene Glycol) Chemistry: Biotechnical and Biomedical Applications*, M. J. Harris, (ed.), Plenum Press, New York, 183–198, (1992).

I. Saiki, et al., "Antimetastatic Activity of Polymerix RGDT Peptides Conjugated with Poly(Ethylene Glycol)," *Jpn. J. Cancer Res.*, 84, 558–565 (May 1993).

L. Sartore, et al., "Enzyme Modification by MPEG with an Amino Acid of Peptide as Spacer Arms", *Appl. Biochem. Biotechnol.*, 27, 45–54, (1991).

S. L. Schor, "Cell Proliferation and Migration on Collagen Substrata In Vitro", *J Cell Sci.*, 41, 159–175, (1980).

D. P. Speer, et al., "Biological Effects of Residual Glutaraldehyde in Glutaraldehyde–Tanned Collagen Biomaterials", *J. Biomed. Mater. Res.*, 14, 753–764, (1980).

M. Stol, et al., "Structural Alterations of p(HEMA)–Collagen Implants", *Biomaterials*, 12, 454–460, (Jul. 1991).

Y. H. Sun, et al., "Synthesis and Characterization of Non Fouling Polymer Surfaces: I. Radiation Grafting of Hydroxyethyl Methacrylate and Polyethylene Glycol Methacrylate onto Silastic Film", *J. Bioactive Compatible Polymers*, 1, 316–334, (Jul. 1986).

R. Tu, et al., "A Preliminary Study of the Fixation Mechanism of Collagen Reaction with a Polyepoxy Fixative", *Intl. J. Artificial Organs*, 16, 537–544, (1993).

P. B. van Wachem, et al., "Biocompatibility and Tissue Regenerating Capacity of Crosslinked Dermal Sheep Collagen", *J. Biomed. Mater. Res.*, 28, 353–363, (1994).

M. C. Woodle, et al., "Versatility in Lipid Compositions Showing Prolonged Circulation with Sterically Stabilized Liposomes", *Biochim. Biophys. Acta*, 1105, 193–200, (1992).

E. A. Woodroof, et al., "Use of Glutaraldehyde and Formaldehyde to Process Tissue Heart Valves", *J. Bioeng.*, 2, 1–9, (1978).

I. V. Yannas, et al., "Cross–Linking of Gelatine by Dehydration", *Nature*, 215, 509–510, (1967).

S. Zalipsky, et al., "Esterification of Polysthylene Glycols", *J. Macromol. Sci,–Chem.*, A21, 839–845, (1984).

S. Zalipsky, et al., "Evaluation of a New Reagent for Covalent Attachment of Polyethylene Glycol to Proteins", *Biotech. Appl. Biochem.*, 15, 100–114, (1992).

BIOSTABLE POROUS MATERIAL COMPRISING COMPOSITE BIOPOLYMERS

FIELD OF THE INVENTION

The present invention relates to porous material useful as wound scaffolds and comprising biopolymers on which have been grafted synthetic polymers and/or monomers.

BACKGROUND OF THE INVENTION

In numerous cases of surgical intervention, it is necessary to replace, complete or strengthen missing or injured tissues. No ideal substitute for connective tissue replacement is currently available. It is known that collagen modifies the morphology, migration, adhesion and, in some cases, the differentiation and growth of cells[1,2]. Different types of collagen (types I, III and IV), gelatin, purified or reconstituted extracellular matrices, glycoproteins such as fibronectin, laminin and vitronectin, fibrinogen/fibrin, composite support containing glycosaminoglycans, basement membrane (Matrigel™), cellulose, chitosan and chitin derivatives can be used to support cell growth[3], and may be used alone or in combination in the porous matrix of the present invention.

To assist wound healing, biocompatible and biodegradable collagen materials may be used. Controlling the rate of biodegradation by crosslinking such implants not only determines the lifetime of the material after application, but may also determine the rate of tissue regeneration[4].

Crosslinking of collagen can be effectively achieved by chemical, radiation and/or dehydrothermal methods. Chemical agents such as glutaraldehyde, hexamethylene-diisocyanate, acyl azide, 1-ethyl-3-(3-dimethylaminopropyl) carbodiimide (EDCI) hydrochloride, N-hydroxysuccinimide, or polyepoxy fixative have been broadly used to create the biological stability of collagen[4–8]. Glutaraldehyde is however an example of crosslinking agents having the disadvantage of releasing toxic components during in vivo degradation[32]. In addition, the introduction of crosslinking agents to the natural crosslinking of collagen can modify the biological properties of collagen.

As previously demonstrated by co-inventor and others[9–12], gamma or electron beam irradiation has been used to stabilize the collagen structure with beneficial results in clinical applications. Besides, ionizing radiation has been successfully used for grafting collagen onto synthetic materials as polyester vascular prostheses for angiosurgery[13] as well as for the preparation of collagen substitutes such as abdominal paries and dura mater[11].

Synthetic polymers have been used to coat surfaces, including biopolymers surfaces or have been conjugated to biopolymers to modify their properties, for various purposes. Polyethyleneglycols (PEGs) which are versatile polymers having amphiphilic (hydrophilic and hydrophobic) properties[33], are used to increase the resistance of proteins to proteolytic degradation. PEGs have been reported to abrogate the immunogenicity of proteins while preserving their biological properties[34, 35]. PEGs were conjugated to various proteins or lipids to produce various delivery systems for drugs, cytokines and enzymes[33,36–39]. Using PEG-modified adenosine deaminase, children who have an adenosine deaminase deficiency were successfully treated[36]. Neither toxic effect nor hypersensitivity reactions were observed. Furthermore, PEGs were conjugated to liposomes significantly prolong their biological properties[40]. More recently, PEGs have been conjugated to pepsinized collagen in solution utilizing succinic anhydride and glutarate reactions[14,15,35].

Previously, only chemically activated PEGs in collagen modification was studied[14,15]. Thus, it was found that PEG-collagen derivatives present more favourable biological properties than non-grafted ones. PEG has been also used as plasticizer of collagen and to enhance resorption and protection of peptide drug[16,17]. Furthermore, poly(2-hydroxyethyl methacrylate) (pHEMA) has been chemically bound to soluble or insoluble collagen crosslinked by glutaraldehyde[18–22]. These polymers are stable against biodegradation and have shown a good biocompatibility without any cytotoxicity[22]. Moreover, a great deal of work has been devoted to the use of PEG and HEMA to create synthetic polymers or graft copolymers. Comprehensive reviews of this literature have been published[23–25].

Recently, we have applied chemical or radiation processing to develop a new family of collagen-based biopolymers. Subsequent modification of collagen is performed by systematically varying the grafting solution compositions using hydrophilic and hydrophobic macromonomers with different chain lengths. These specific chemical- or radiation- modified composite materials could be selected to fulfill special biological and medical needs.

It will be therefore appreciated that composite collagen material containing different proportions of synthetic polymers and/or monomers and having different biological properties can be obtained by using chemical or radiation techniques.

The U.S. Pat. No. 4,840,851 describes the use of PEG in the coating of surfaces as protein-repellent, by keeping a freely movable polyethylene oxide chain, unsaturated, and which will not take part in the crosslinking; this part of the PEG derivative molecules is usually a conventional etherified end. The other end is the OH-terminus esterified with a compound having an ethylenically unsaturated group. Radiation has been used and crosslinking is achieved by allylic, acrylic or methacrylic groups. No suggestion is made in this patent of a porous collagen product which, when impregnated with PEG and/or PHEMA and irradiated, has a stable porosity.

The U.S. Pat. No. 4,871,490 describes hydrogels made by mixing natural and synthetic polymers, and optionally a plasticizing agent, in water, this mixture being poured in a mould and cured. No porous material is suggested. The making of a composite collagen sponge cannot be deduced from this reference because curing such a mixture will not result in a porous structure but in a compact one. Therefore, there is no suggestion of impregnating a collagen sponge with PEGs which will produce a stabilized porous material by chemical or radiation methods.

The U.S. Pat. No. 4,978,298 teaches a collagen sponge which is crosslinked with carbodiimide. The composite sponges do not lose the biological properties of collagen (and of added connective tissue factor) and show a decreased inflammatory response. Even though the composite sponges are capable of supporting ingrowth of fibroblasts, there is no indication of a bio-stable porosity.

The U.S. Pat. No. 5,290,548 teaches the coating of implants which precludes adhesion and spreading of cells and will not encourage colonization by infiltration and fixation of cells.

The U.S. Pat. No. 5,162,430 teaches collagen-polymer conjugates. A polymer like MPEG is activated by reaction with a linking group and such an activated polymer is then reacted with the free amino groups of collagen. The conjugated material is taught as being useful as an implant having an increased tensile strength as well as a longer residence time in the body than a non-conjugated crosslinked collagen implant. This reference does not exclude the use of fibrillar collagen and does not exclude colonization of implants by cells. However, this reference does not teach a composite collagen sponge having a stable porosity.

The patent publication EP 568,334 teaches collagen sponges made by soaking gelatin sponges in a mixture of collagen and of a pharmacologically active ingredient enhancing and promoting wound healing. No sponge made of a composite collagen-polymer material and having a stable porosity is neither disclosed nor suggested in this reference.

In tissue repair mechanism, e.g. after wounding or surgery, the cells contributing to new tissue reconstruction need a matrix supporting cell growth. Sponges made of collagen are provided as matrices supporting cell growth. However the pores of these sponges through which fibroblasts infiltrate are prone to collapse shortly after their implantation. Indeed the pores do not remain stable for a time sufficient for fibroblast colonization.

Therefore, there is clearly a need for sponges containing biopolymers capable of supporting cell growth which have a stabilized porosity, allowing for colonization of fibroblasts, as well as an improved resistance to proteolysis.

STATEMENT OF THE INVENTION

The present invention relates to a biomaterial of a stable porosity which comprises a porous biopolymer matrix into which is conjugated a polyethylene molecule having a substituted ether end and an ester, thioester or imino end taking part to the conjugation with the biopolymer.

In a preferred embodiment, the polyethylene molecule has the following formula:

A—O—(CH$_2$—CH$_2$—O)$_m$—(CH$_2$)$_n$—Z wherein:

m is an integer comprised between 2 and 500;
n is an integer comprised between 1 and 7;
A is selected from the group consisting of:
   B—CR=CH—, wherein R is hydrogen or a lower alkyl, and B is hydrogen, carboxy, hydroxy, aldehyde, NH$_2$— or SH—;
   cyanuric chloride or hydrogen cyanide;
   $_2$OS—X—CH$_2$—, wherein X is void or a linear, branched or aromatic group of 1 to 6 carbon atoms;
   D—OOC—(CH$_2$)$_o$—, wherein o is an integer comprised between 1 to 7, and D is hydrogen, azide, methyl,—NH—NH$_2$—, an anhydride, a mixed anhydride or an activated ester;
   —N—(CH$_2$)$_o$—, wherein o is an integer comprised between 1 to 7;
   —S—(CH$_2$)$_o$—, wherein o is an integer comprised between 1 to 7;
Z is selected from the group consisting of:
   hydrogen;
   —FGE wherein F is O$^-$, N$^-$ or S$^-$, G is hydrogen, a lower alkyl, a cycloalkyl of 1 to 7 carbon atoms or —C(O)—I, wherein I is a reactive group of a pharmaceutical agent, and E is hydrogen or a lower alkyl; and
   —C(O)—JE, wherein J is hydrogen, a lower alkyl, a cycloalkyl of 1 to 7 carbon atoms or —O—K, wherein K is a reactive group of a pharmaceutical agent, and E is hydrogen or a lower alkyl.

In another preferred embodiment, the biopolymer is selected from collagen, crosslinked gelatin, fibronectin, laminin, vitronectin, fibrinogen/fibrin, glycosaminoglycans, Matrigel™, cellulose, chitosan and chitin.

In a particular embodiment, the biopolymer is collagen, most preferably type I collagen.

Practical examples will show a composite collagen porous material wherein A is a) methacrylate, and conjugation is performed by gamma radiation and b) cyanuric chloride and conjugation is performed by chemical means. Two types of polyethylene glycol have been used, PEG-750 and -5000, in which cases m is an integer comprised between 7 to 45, n is 1 and Z is hydrogen.

When it is intended to conjugate a pharmaceutical agent to the composite porous material, such a pharmaceutical agent may be an antibiotic or a growth factor. Such a growth factor may be selected from the group consisting of: FGF, EGF, TGF, PDGF, TNF, IGF, CSF, NGF, heparin binding growth factor, interferons, erythropoeitin, interleukins and tissue activating peptides.

It is also another aspect of this invention to provide a process of preparing a composite porous biomaterial which comprises the steps of:
   a) dispersing a biopolymer in water;
   b) freezing the dispersion at about −10° to about −20° C.;
   c) freeze-drying the dispersion at a pressure reduced under about 100 millitors at a temperature of about −30° to about 0° C.;
   d) obtaining a porous biomaterial having channels of an average pore size of from about 50 μm to about 250 μm;
   e) conjugating the biopolymer by impregnating the same with a polyethylene molecule as defined in the above formula at room temperature;
   f) rinsing the conjugated porous biomaterial; and
   g) freeze-drying or air-drying the conjugated porous biomaterial to obtain a composite sponge or film, respectively.

DESCRIPTION OF THE PRESENT INVENTION

The present invention relates to porous material useful as temporary wound scaffolds. The porous material consists of sponge-like matrices with a porous and fibrillar structure which can be obtained by freeze-drying a biopolymer dispersion, preferably a collagen dispersion. The biopolymer sponges are then impregnated with a solution of PEG derivatives and allowed to react therewith to obtain composite matrices which have a stable porosity. These matrices can also be used as a support for biologically active molecules to improve wound healing and to reduce wound infection (growth factors and antibiotics, for example). In addition, these composite matrices can be implanted and used as drug delivery systems (for antimitotic drugs, for example).

Biomaterials, particularly those made of biological polymers should be substantially non-toxic, non-immunogenic, and stable for a period of time necessary to encourage colonization by cells involved in tissue reconstruction before they are degraded and resorbed by the recipient organism.

A first series of porous material obtained in accordance with the present invention results from the chemical conjugation of a PEG derivative, particularly an activated synthetic polymer, more particularly cyanuryl-activated PEG, with biopolymer sponges, such as collagen sponges.

A second series of porous material obtained in accordance with the present invention results from the use of radiation technique in the preparation and in the simultaneous sterilization of the synthetic polymer- and/or monomer- grafted biopolymer sponges, particularly MPEG-grafted sponges or MPEG-pHEMA-grafted sponges, wherein the biopolymers may be collagen.

These materials have been characterized with regard to their physico-chemical properties and their in vitro and in vivo biocompatibility.

Various modifications can be carried out on the molecule of PEG, the resulting modified PEGs having the following general formula:

A—Y—(CH$_2$CH$_2$O)$_m$—(CH$_2$)n—Z wherein m+n is an integer comprised between 2 and 500;

Y is —O—, —S— or —N—;

A is selected from the group consisting of:
B—CR=CH—CO—, wherein R is hydrogen or a lower alkyl, and B is hydrogen, carboxyl, hydroxyl, aldehyl, NH$_2$— or SH—;
cyanuric chloride or hydrogen cyanide;
$_2$OS—X—CH$_2$—, wherein X is void or a linear, branched or aromatic group of 1 to 6 carbon atoms;
D—OOC—(CH$_2$)$_o$—CO—, wherein o is an integer comprised between 1 to 7, and D is hydrogen, carbodiimide azide, methyl, —NH$_2$—NH—, —HN—C=N—, an anhydride or a mixed anhydride;
an activated ester;
—N—(CH$_2$)$_o$—, wherein o is an integer comprised between 1 to 7; and
—S—(CH$_2$)$_o$—; and Z is selected from the group consisting of:
hydrogen;
—EFG, wherein E is —O—, —N— or —S—, F is hydrogen, a lower alkyl, a cycloalkyl of 1 to 7 carbon atoms or —C(O)—I, wherein I is a reactive group of a pharmaceutical agent, and G is hydrogen or a lower alkyl; and
—C(O)—JG, wherein J is hydrogen, a lower alkyl, a cycloalkyl of 1 to 7 carbon atoms or (O)K, wherein K is a reactive group of a pharmaceutical agent.

Even though the presently disclosed invention provides detailed examples involving MPEG-750 and 5000, the skilled reader will readily appreciate that variations may be made in the selected molecular weight, without departing from the present teachings. The contemplated variations can be brought as follows by:

Varying the chain length of PEG (m). We have observed in the course of our experiments that the length of PEG chain plays an important role in the structure-activity relationships in modifying collagen (shorter the MPEG chain easier is the induction of tissue ingrowth in the collagen materials). This observation could involve two phenomena (i) less steric hindrance of the molecules and easier reaction of several molecules on the same protein until or (ii) easier diffusion of small MPEG derivatives inside sponges. Several MPEG derivatives having a wide range of molecular weights (300–10000) can be prepared and added to sponges;

Varying the nature and the length of the linking arm of MPEG (o). It is of outmost importance to control the degradation of collagen derivative in vivo to insure proper wound healing. The residence time can be increased by impeding the collagenase activity on the modified collagen or the reaction of an esterase on the removal of MPEG on collagen. Such a control of degradation could be obtained by the proper selection of the molecular moiety linking PEG to collagen. For example, it is well known that esters of maleic, glutaric and succinic acids have very different hydrolysis rates (toward esterases). Such esters will modify the rate of MPEG removal from collagen and therefore the rate of the action of collagenase. These esters may have 1 to 8 carbon atoms. Otherwise, in the radiation method, no linking arm may be necessary to provide protection towards enzymes.

Varying the nature of the activating group responsible for the conjugation of MPEG to collagen (A). This part of the molecule is also important to insure proper conjugation of the PEG derivatives to collagen. In our preliminary experiments, we used cyanuryl chloride which worked nicely. However, this molecule is suspected for some inflammatory response, and cytotoxicity when not removed completely. Therefore, alternatives have to be developed. We are actually using the hydrosoluble carbodiimide EDCI to conjugate acid terminated MPEG (CH$_3$ (OCH$_2$CH$_2$)$_m$OC(O) CH$_2$COOH) to collagen. However, for easiness of manipulation, the pH and the rate of conjugation, several types of activated esters such as N-hydroxysuccinimide ester or pentafluorophenol ester can be prepared;

Varying the nature of the terminating group of PEG (Z). In MPEG, that group is a methyl. We strongly believe that the nature of this group could play a crucial role in cell interactions with collagen. For example, the substitution of methyl by a carboxyl (negative charge) or an amino (positive charge) will strongly modify the properties of the collagen towards cells. Furthermore, these groups could be used to conjugate growth factors or polyamines and pharmaceutical products such as antibiotics, defined by I and K in the above formula. A mono benzyl derivative of PEG can be made for example.

Surprisingly and in accordance with the present invention, the porous materials have been shown to have a stable porosity, which greatly reduces collapsing of the pores and therefore allows for colonization of the cells participating in the reconstruction of tissue during the period after which these materials are resorbed.

The present invention will be described hereinbelow in further details in the following Examples and appending Figures, which purpose is to illustrate the present invention and not to limit its scope:

BRIEF DESCRIPTION OF THE FIGURES

FIGS. 4A through 4F. Histological sections of collagen sponges having the FTIR spectra of FIG. 3 after subcutaneous implantation for 15 days. Collagen sponges were treated using gamma irradiation techniques in the presence of MPEG-750 (A); MPEG-5000 (B); MPEG-750-pHEMA (C); MPEG-5000-pHEMA (D); pHEMA (E); and without any modification (F). Note in A the presence of adipocytes (arrowhead) within the porous structure, and in F the collapsed porous structure (arrows) that occurred by 15 days. At that period, the MPEG and/or pHEMA treated sponges did not exhibit collapsed pores.

MATERIALS AND METHODS

Materials

Methoxy poly (ethylene glycol)s (MPEGS) with average molecular weight 750 and 5000 from Sigma Chemical Co. (St Louis, Mo.) were used as received in the present study. These average molecular weights of MPEGs have been chosen, but others can be used. 2-hydroxyethyl methacrylate (HEMA) from Aldrich Chemical (Milwaukee, Mich.) was distilled at 69° C. under 5 mm Hg pressure, saturated with $N_2$ and stored at 4° C. Cyanuryl chloride is purchased from Aldrich Chemical.

Collagen type I was extracted from adult hide using a series of acid dispersions and salt precipitations. We have modified known techniques to extract large quantity of insoluble collagen fibers from bovine skin. Briefly, freshly hair-removed bovine skin (adult hide) is extensively rinsed in cold water overnight with several changes. The dermal part is separated from the epidermal and subcutaneous parts. Dermal part is then cut in small pieces. The small pieces are then soaked in acetic acid (0.5N) under constant homogenization in cold room for 24 hours. A stirrer equipped with a three-bladed paddle is used for the homogenization procedure. The swollen pieces are then passed through a sieve (mesh #7) which is extensively rinsed in distilled water. The first collagen that goes totally through the sieve is considered as soluble collagen which is then discarded. The remaining swollen pieces retained by the sieve are considered as insoluble collagen (type I). This insoluble collagen will be used to conceive the collagen-based materials. Collagen is then trimmed using a blender in the presence of crushed ice. Non-dispersed collagen is collected through the sieve and the homogenization procedure is repeated until all swollen pieces of collagen are completely dispersed (forming a dispersion of coarse fibrils and fibers).

The collection of collagen is then salt precipitated (crystal NaCl 2M) for 2 hours in cold room. The salt-precipitated insoluble collagen is collected and then immersed in acetone for a period ranging from a few hours to overnight under orbital agitation. Acetone-washed collagen is passed through the sieve and left to evaporate for 10 minutes. Collagen is then dispersed in acetic acid solution (0.5N) and homogenized by using a stirrer equipped with a three-bladed paddle for at least 2 hours in cold room in order to evaporate residue of acetone. The final dispersion (about 0.5% w/v) is then dialyzed in cold room against acetic acid (0.5N) to remove NaCl residues (2–3 times) and then dialyzed against distilled water containing 5:1000 (v/v) chloroform solution in the first bath. The second, third and fourth baths only consist of distilled and deionized water. Collagen is then lyophilized and stored in aliquots at a temperature ranging from −70° to −10° C. until used for producing the collagen sponges.

The extracted and purified collagen is specific of type I collagen and has been characterized by gel electrophoresis where specific bands alpha 1 and 2, and beta are observed. It has also been characterized by HPLC where the ratios of amino acids were specific of type I collagen. No other proteins were detectable by both methods. The observation under a light microscope and using specific stains for collagen demonstrates a native collagen similarly stained as in a normal tissue. On the other hand, long fibrils and bundles of fibrils were observed with periodicity as seen in normal connective tissue by electron microscopy. The implantation of this collagen on animals did not induced foreign body reaction and no obvious inflammatory reaction was observed.

For sponges, collagen was dispersed uniformly at a concentration varying from 0.3 to 1% concentration (w/v) in distilled and deionized water. After deaeration, the collagen dispersion was frozen at a low temperature ranging from −30° to 0° C. and then lyophilized in a freeze-drier.

Methods and Observations

A. Chemical Methods:

Collagen sponges impregnated with and conjugated to cyanuryl-activated PEG

MPEG was activated with cyanuric chloride according to the method of Abuchowski et al.[34]. Firstly, PEG-cyanuryl was prepared in a mono-substitution reaction and extensively purified by numerous cycles of solubilization in anhydrous benzene and precipitation with petroleum ether or hexane. Secondly, after the conjugation of PEG-cyanuryl chloride to collagen, the conjugate was extensively washed with water to remove all unreacted water-soluble by-products of the reaction which were mainly $Cl^-$, unreacted PEG-cyanuryl chloride and its eventually hydrolyzed derivatives. Solutions were prepared at concentrations of 5, 25 and 50 mg/mL activated PEG in 4% w/v sodium bicarbonate solutions at pH 8.0. The 5, 25 and 50 mg/mL activated PEG solutions corresponded to concentrations of 1, 5 and 10 mg activated PEG per mg of collagen (1:1; 5:1; and 10:1 w/w) respectively. Two average molecular weight PEGs, high (PEG-5000) and low (PEG-750), were conjugated to type I collagen at room temperature as follows:

PEG-modified collagen

Collagen materials were immersed in extemporaneously prepared PEG-cyanuryl chloride solutions at room temperature. For collagen sponges, this procedure was specifically done under vacuum (>100 millitors) to remove the air trapped within the pores. Sponges were then immersed in the activated PEG solutions. The latter procedure was used because the collagen sponge was a compact material with air trapped in its structure. Nevertheless, this procedure carried out a gradient of conjugation of PEG decreasing from the outside to the inside of sponges. Specimens were then soaked with intermittent agitation in the aqueous solution for 2 hours at room temperature. After 2 hours, specimens were immersed in water, rinsed extensively with water and then freeze-dried or air-dried for the sponges and films, respectively. Untreated collagen materials were used as control.

For cell culture and animal implantations, collagen materials were aseptized by immersion in 70% isopropanol and then rinsed in sterile HEPES (0.05M)—NaCl (0.1M) solution, followed by an immersion in sterile Hank's balanced salt solution overnight to remove any residual alcohol.

Morphology of sponges

Scanning Electron Microscopy (SEM) was performed on freeze-dried sponges that were directly sputter-coated with gold-palladium and observed under JEOL SEM.

SEM observations of the surface of sponges prior implantation showed a wide range of pore sizes. The porosity on the surface of non-treated sponges was close to that observed on PEG-conjugated sponges. The porosity of sponge surface was slightly increased as the initial concentrations of PEG. At high magnification, collagen fibrils were present and distinct on all surfaces of the specimens.

Fourier transform infrared spectroscopy

Infrared spectra were recorded with a Nicolet Magna-550 Fourier transform infrared(FTIR) spectrometer (Nicolet Instrument Corp., Madison, Wis., USA) with a DTGS detector and a germanium coated KBr beamsplitter. One hundred scans were routinely acquired with an optical retardation of 0.25 cm, triangularly apodized and Fourier transformed to yield a 4 cm$^{-1}$ resolution. The attenuated total reflectance (ATR) mode has been used in order to record the infrared spectra of the collagen sponges with a Split Pea attache (Harrick Scientific Corp., Ossining, N.Y., USA) equipped with a Si hemispherical, 3 mm diameter internal reflection element (IRE). The ratio of the amount of PEG with respect to collagen was monitored by dividing the areas under the curve situated between 1000 and 1200 cm$^{-1}$ by those between 1490 and 1750 cm$^{-1}$. The two latter infrared region ranges corresponded to the most intense infrared features of PEG and to the amide I and amide II peaks of peptidic bounds within collagen respectively.

Figure 1:
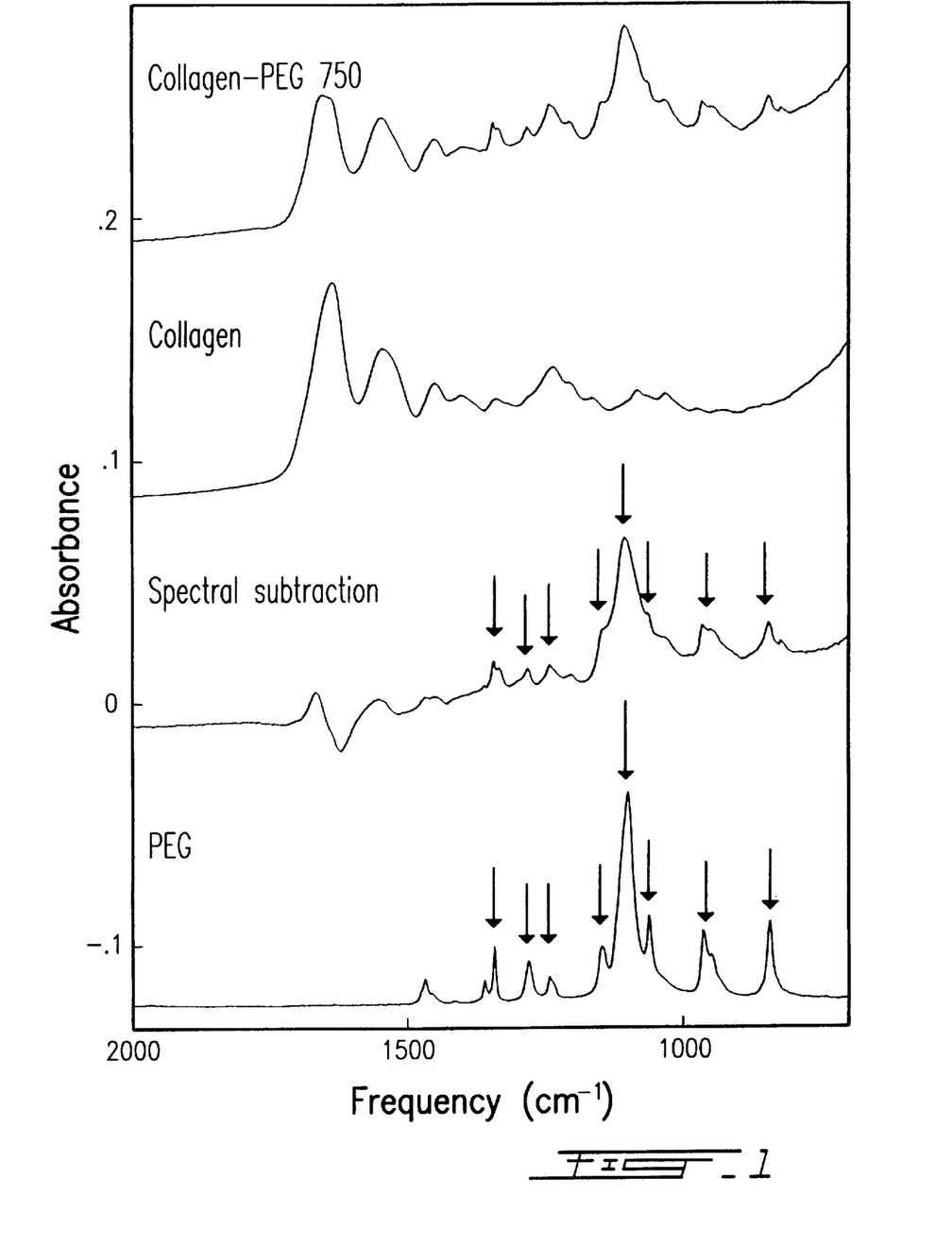
FIG. 1. FTIR-ATR spectra of PEG-750-modified collagen (10:1 w/w), collagen and PEG. The spectra of collagen alone was subtracted from that of PEG-collagen to highlight PEG present in collagen after conjugation of cyanuryl-activated PEG as shown by the arrows.

FIG. 1 clearly shows that PEG is present into the modified collagen sponges. For example, the infrared spectrum of the PEG-750-collagen (10:1 w/w) sponge exhibited the characteristic of PEG as shown after subtracting the spectral contribution of collagen alone from the spectrum of the PEG-750-collagen (10:1 w/w) sample. Comparison of this spectral subtraction with the spectrum of PEG unambiguously demonstrated that the infrared features of PEG were present in the spectrum of PEG-750-collagen (10:1 w/w) spectrum as highlighted by the arrows on the FIG. 1.

In order to quantify the amount of PEG present into the PEG-modified collagen sponges, the infrared ratio $A_{PEG}/A_{Collagen}$ was determined. Since collagen also contributed to the infrared absorbance in the 1000–1200 cm$^{-1}$ domain, the ratio of the areas under the collagen spectrum in the 1000–1200 cm$^{-1}$ and 1490–1750 cm$^{-1}$ regions was calculated and subtracted from the $A_{PEG}/A_{Collagen}$ ratios determined for the PEG-collagen sponges. Areas under the curve were determined using GRAMS/386™ (Galactic Industries, Salem, N.H., USA) . The infrared ratio $A_{PEG}/A_{Collagen}$ is directly related to the PEG/collagen ratio, the proportionality constant being the ratio of the molar absorptivity constants of PEG between 1000 and 1200 cm$^{-1}$ and those of collagen between 1490 and 1750 cm$^{-1}$. This ratio was plotted as a function of the initial concentration of the PEG solutions used to perform the reaction between PEG and collagen. PEG was present into the collagen structure for all PEG-collagen samples investigated. However, the PEG/collagen ratio into the sponges was not obviously related to the initial concentration of PEG. A small and almost equivalent amounts of PEG-750 seemed to be present into collagen structure when initial PEG concentrations of 5 and 25 mg/ml were used. In contrast, an initial PEG concentration of 50 mg/ml promoted an important increase of the PEG amount into the PEG-750-collagen sponge. The insertion of PEG-5000 into the collagen structure exhibited a different behaviour than that observed with PEG-750. The ratio of PEG present in collagen structure slightly increased proportionally to PEG present in the initial solution. Finally, the two lower initial PEG-750 and PEG-5000 concentrations both resulted in a low level of insertion into the collagen structure. On the other hand, a higher initial PEG-750 concentration (50 mg/ml) lead about 5.5-fold increased level of insertion into the collagen structure when compared to that observed for PEG-5000.

Collagenase Assay

Freeze-dried collagen sponges were immersed in collagenase (type IA from Clostridium histolyticum, Sigma Chemical Co., Missouri) neutral solution (pH 7.2–7.4) containing TRIS buffer (25 mM) and $CaCl_2$ (10 mM) at a concentration of 250 units of collagenase per mg of collagen. Specimens were incubated at 37° C. and observed at 5 minute intervals during the incubation. The incubation period that resulted in complete disappearance of collagen sponges was considered relative to the degradability of sponges.

The degradation of PEG-conjugated collagen sponges by collagenase was delayed in comparison to untreated sponges (Table 1). There was no significant difference between low and high molecular weight PEG-conjugated sponges except an increase in collagenase resistance at low concentration of PEG-5000.

Fibroblast Cell Cultures

Collagen films were made either on glass cover slips for SEM observations or directly in wells of 24 multiwell plates for measurements of cell growth. Passaged human foreskin dermal fibroblasts were seeded onto collagen films at a low cell density of $1 \times 10^3$ cells/cm$^2$ to determine cell growth and at a high density of $1 \times 10^4$ cells/cm$^2$ for SEM observation. Cells were cultivated in Dulbecco's Modified Eagle Medium (Sigma Chemical Co., St Louis, Mo.) supplemented with 5% fetal bovine serum (GIBCO/BRL, Burlington, Ontario) and antibiotics (100 I.U/ml penicillin, 100 $\mu$g/ml streptomycin, and 25 $\mu$g/ml amphotericin B; GIBCO/BRL, Burlington, Ontario). Cells were grown in an incubator at 37° C. under water saturated atmosphere in 5% $CO_2$.

At 24, 48, and 72 hours and 7 days, cell growth was measured by cell counts directly on low cell density-seeded films using a supravital DNA stain (Hoechst 33342; Polysciences, Inc., Worrington, Pa.). A 10 $\mu$g/ml Hoechst 33342 solution in culture medium was incubated for 5 minutes. Specimens were then rinsed in phosphate buffered salt solution, and were observed at 25× under epifluorescence using an excitation filter for U.V. (365 nm). Nuclei of cells were randomly counted at different times post-seeding.

At 7 days, high cell density-seeded films were fixed with a solution of glutaraldehyde(2.5% in 0.1M cacodylate buffer at pH 7.3) for SEM observation. After rinsing with cacodylate solution, they were dehydrated using increasing ethanol gradients. Hexamethyldisilizane (Polysciences, Inc., Worrington, Pa.) was used in place of the $CO_2$ critical point drying procedure according to the manufacturer. Specimens were mounted on a stub and gold sputter coated before observation under SEM.

Cell growth was not significantly modified by the presence of PEG conjugated to collagen when compared to cells grown on collagen alone. At 72 hours, cell growth was slightly increased on collagen films in comparison to treated films. However, by 7 days, there were no significant differences between treated and non-treated collagen films.

On PEG-conjugated collagen films, high cell density seeding induced confluence within 5 to 7 days. Confluent cells were broadly spread onto the surface of collagen films. No detached cells were observed. They were elongated at confluence and tightly juxtaposed to each other. The morphology of cells on non-modified films behaved in a close manner than that on PEG-conjugated collagen films.

Subcutaneous Implantations

Subcutaneous implantations of sponges were performed in mice under anesthesia. Surgery were conducted under sterile conditions according to the guidelines of the Canadian Council for Animal Care and after approval by the Institutional Animal Care Committee. Two subcutaneous pockets on each flank were made by a medial incision on the back of each animal. Collagen sponges (1 cm square) were then inserted in the pockets.

At 7, 15 and 30 days post-implantation, specimens were collected and fixed in formaldehyde and processed for histological evaluation. Tissue sections were stained with hematoxylin-phloxin-saffron (HPS) for microscopic observations. For each period and each PEG-modified collagen sponge, three specimens were implanted.

HPS stained tissue sections were used to quantify the relative porosity of sponges in two-dimensions. Specimens were observed under a microscope connected to a video camera at a magnification of 160×. Using a computerized image analysis system (MEG X, Bioquant IV, Minneapolis, Minn.), three measurements were made for each specimen at different times after implantation. Under constant lower and upper levels of image enhancement, thresholds were determined to exhibit only the surfaces occupied by the pores underlined by the sponge collagen fibers. On each tissue section, the surfaces occupied by the pores of the sponge were determined quantitatively. Data were statistically compared using the student's t-test at $p<0.01$.

Figure 2A:
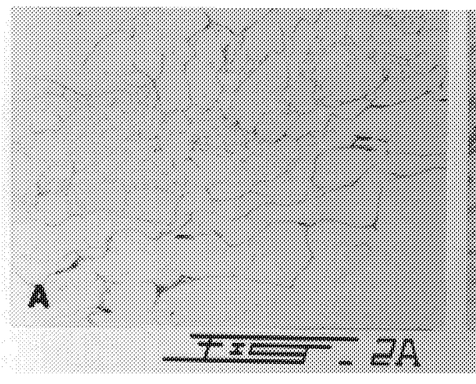
FIGS. 2A through 2D. Histological observation of collagen sponges having the FTIR-ATR spectra of FIG. 1 after subcutaneous implantations in mice. Collagen sponges had a porous structure prior to implantation (A). Non-modified sponges collapsed by 15 days (B). In the presence of low (PEG-750; D) and high (PEG-5000; C) average molecular weight PEGs, collagen sponges were infiltrated by fibroblasts and the porous structure remains by 30 days. Tissue infiltration within large pores was observed when activated PEG-750 was conjugated to collagen (D) Bar=1 μm.
Figure 2B:
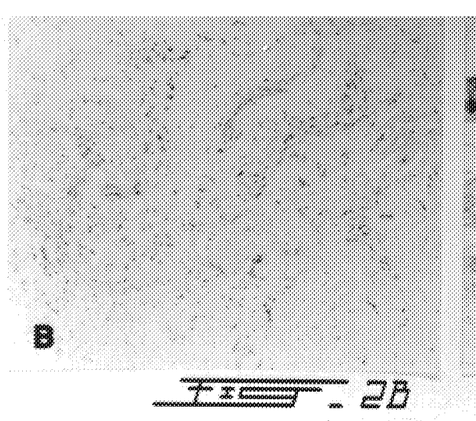
Figure 2C:
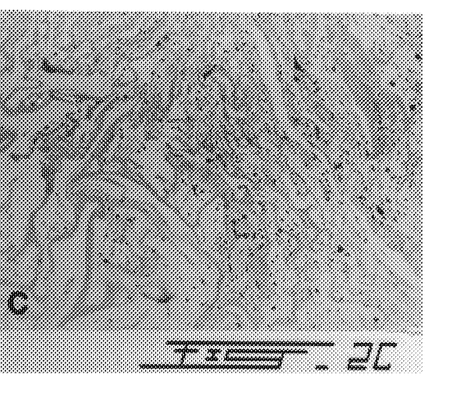
Figure 2D:
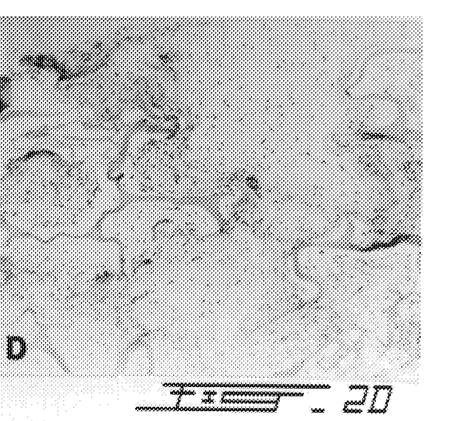

Non-modified sponges were collapsed by day 15 with few fibroblasts between the collagen fibers. Non-modified sponges were still present 30 days after the implantation (FIG. 2). In FIG. 2D, PEG-750-conjugated collagen sponge was well infiltrated by tissue ingrowth by 30 days. Modified collagen sponges remained porous for at least 30 days. Large pores were observed in sponges, particularly with high concentrations of PEG-750. On PEG-5000 conjugated collagen sponges, the size of the pores was reduced as a function of time post-implantation when compared to those with PEG-750. Quantitative analysis showed significant differences in pore areas between PEG-conjugated sponges and non-modified sponges on day 7 and 15. By day 30, the pore sizes were significantly increased in PEG-750 conjugated sponges as compared to the non-modified samples. Prior to implantation, the values of pore area of PEG-750 conjugated sponges were close to those found at 30 days ($p<0.05$). By 30 days, no significant difference was observed between PEG-5000 conjugated sponges and non-modified sponges. At all the periods observed, no significant difference in pore areas was noticed between the initial concentrations of PEG introduced onto collagen.

Radiation Methods

Collagen sponges impregnated with MPEG and/or pHEMA and irradiated:

Aqueous solutions of MPEG at concentrations ranging from 0.3% to 6% w/v or combination of these solutions with HEMA at concentration of 1.5% v/v in each mixture were prepared. The aqueous solutions of pure HEMA at concentration from 1.0% to 3% v/v were also used. The pH of the solutions was kept constant at 8.2 by addition of sodium carbonate/bicarbonate buffer.

Collagen sponges were soaked (under vacuum 100 millitors) with appropriate solutions in the amounts corresponding to the sorption capacity of the sponge. Any residual solution on the surface of sponge was wiped off with filter paper. Then sponges were weighed, sealed in polyester bags (Kapak Corp., Minneapolis, Minn.) and irradiated in air at room temperature.

Irradiation was carried out in $^{60}Co$ gamma source with doses from 20 kGy to 25 kGy. The dose rate, as determined by means of a Fricke dosimeter with $G(Fe^{+3})=15.6$, was 1.4

Gys$^{-1}$. After irradiation, the samples were rinsed in water or in water with ethanol (1:1) (sterile conditions) to extract residual MPEG or low molecular weight PHEMA. These specimens were then submitted to biological investigations. Control sponges were irradiated and processed as the composite ones.

Gravimetric analysis

To establish the extent of stabilization, radiation modified collagen by MPEG was soaked for 24 hrs at 25° C. in an excess of water (1:1000). Swollen samples were filtered off, dried with residual water by filter paper and weighed. Drying process was maintained at 0° C. for 24 hrs in a freeze-drier.

The grafting yield of collagen was determined gravimetrically by using the relation Grafting yield $$\text{Grafting yield} = \frac{W_g - W_0}{W_0} \times 100 \qquad (1)$$

where:

$W_g$=dry weight of grafted sponge (g)
$W_0$=initial dry weight of sponge (g)

The amount of solution (corresponding to monomer) which penetrated into the sponge or water uptake in grafted materials were calculated by the following equations:

$$\text{Water content \%} = \frac{W_w - W_g}{W_g} \times 100 \qquad (2)$$

$$\text{Solution content \%} = \frac{W_s - W_0}{W_0} \times 100 \qquad (3)$$

where:

$W_s$=wet weight of soaked sponge before irradiation (g)
$W_w$=wet weight of sponge grafted and swollen in water (g).

The grafting yield of MPEG onto collagen was relatively low and reached a maximum of 9.0% (Table 2). It should be noted that the detectable amount of grafting at this low level was very small and the grafting yield obtained by weight also contained considerable error. Despite this error, gravimetrical method allows the evaluation of the trend of changes. The grafting yield remained practically constant as the concentrations of MPEGs in sponges increased from 10 mg to 120 mg per 100 mg of collagen. However, the degree of swelling in water progressively decreased as both MPEG concentrations and molecular weights increased(Table 3). Besides, the degree of swelling for all grafted sponges was much lower, about 60% in comparison to non-grafted ones. This behaviour manifests that gamma irradiation noticeably induced crosslinking and/or binding of polymers to collagen, forming composite materials.

Fourier transform infrared spectroscopy (FTIR)

FTIR spectroscopy has been used to monitor the chemical modifications of the collagen structure at the molecular level following interaction with hydrophilic polymers and/or irradiation. Infrared spectra were recorded as described above in the chemical method.

Irradiation of MPEG promotes a broadening and a frequency shift of all the infrared features observed in its spectrum indicating that irradiation induced a complex molecular reorganization into the MPEG structure. In addition, this modification seems to be more important for the lower molecular weight polymer since the irradiated MPEG-750 infrared spectra clearly exhibits more modifications than what is observed in the case of MPEG-5000.

Figure 3:
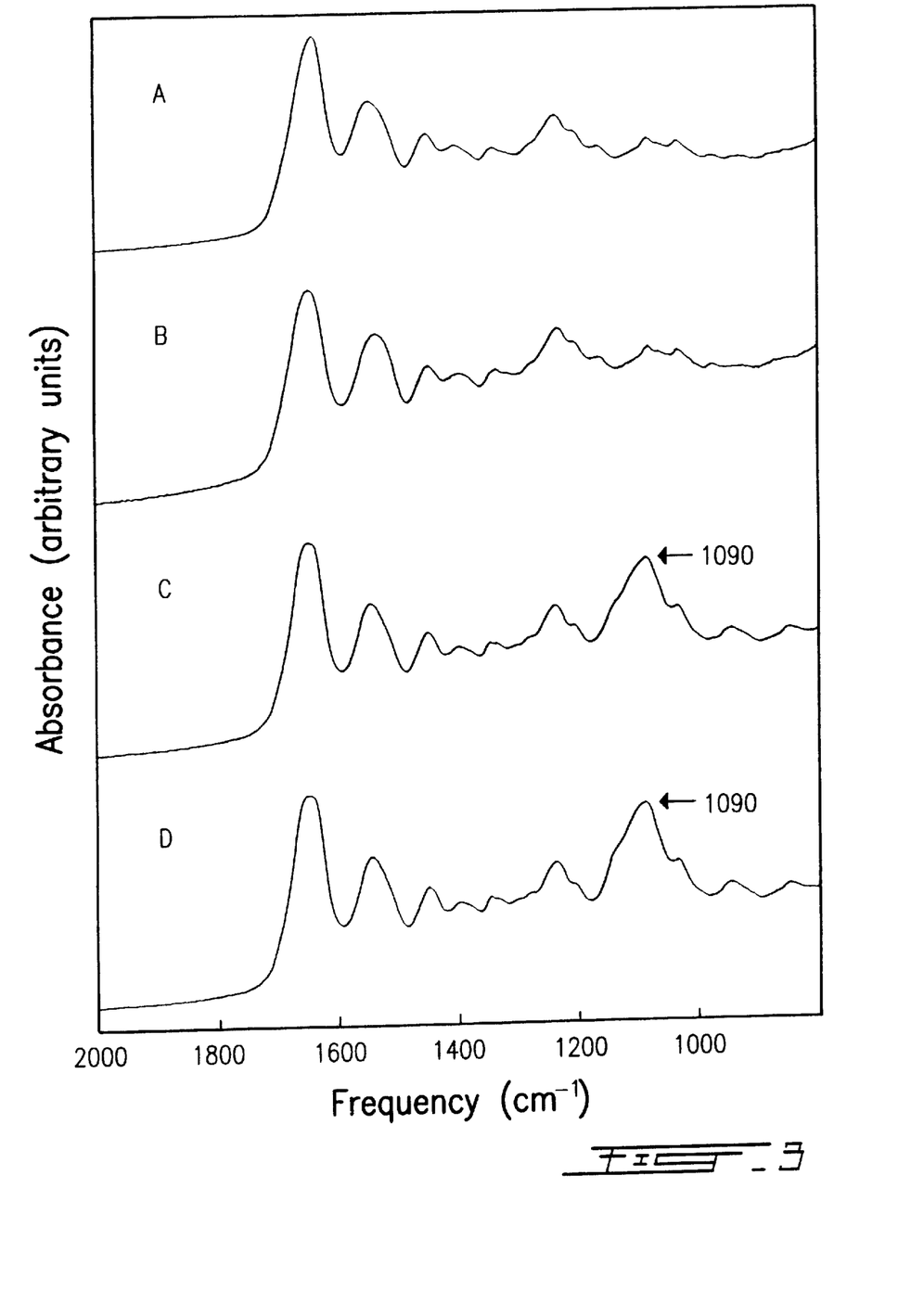
FIG. 3. FTIR spectra of collagen sponges. Collagen alone (A), irradiated collagen (B), irradiated MPEG-5000-collagen (C) and irradiated MPEG-750-collagen (D).

The infrared spectra of collagen, presented in FIG. 3A, shows typical features of proteins known as the amide I, amide II and amide III bands located at 1636, 1540 and 1237 cm$^{-1}$ respectively. A comparison of this spectrum with that of irradiated collagen (FIG. 3B) shows no major modifications since both spectra are almost superimposable. On the other hand, the infrared spectra of irradiated MPEG-5000-collagen and irradiated MPEG-750-collagen sponges (FIG. 3C and 3D) exhibits, in addition to the collagen infrared features, a band located at 1090 cm$^{-1}$, as observed in the infrared spectra of irradiated MPEG solutions. These results unambiguously demonstrate that irradiated MPEG is still present within the collagen structure even after an extensive washing with water.

In order to get more precise information about the secondary structure of collagen, Fourier deconvolution has been performed in order to increase the resolution between infrared features due to the different secondary structures found in collagen. In addition to the characteristic absorption frequency of the β-sheet conformation at 1636 cm$^{-1}$, weaker components are observed at 1660 and 1694 cm$^{-1}$. The 1660 cm$^{-1}$ feature has been previously assigned to the a-helix structure while the peak observed at 1694 cm$^{-1}$ is similar to a β-sheet structure. FTIR is particularly well suited to qualitatively probe changes of the collagen secondary structure due to modifications in the chemical environment of the protein. The frequencies of the amide I and amide II bands, due to vibrations of the peptidic bounds of proteins, are indicative of the secondary structure adopted by these molecules. The amide I band of collagen is centered at 1636 cm$^{-1}$ that is a characteristic of β-sheet structure of proteins. There are also modifications of the shape of the amide I feature upon that irradiation of collagen or irradiation induced interaction of MPEG with collagen.

The deconvoluted spectra of irradiated collagen without any polymer shows a slight increase of the content of the helix structure of the collagen as observed by the increase of the 1660 cm$^{-1}$ infrared feature. On the other hand, a greater amount of helical structure is found in the MPEG-collagen sponges exposed to irradiation. In this latter case, the modification of the secondary structure collagen does not seem to depend on the molecular weight of MPEG since both infrared spectra of irradiated MPEG-5000-collagen and irradiated MPEG-750-collagen sponges exhibit a very similar amide I band, meaning that the secondary structure of collagen in these two latter samples is very similar.

The interaction of pHEMA with collagen has also been investigated by FTIR. The infrared spectra of irradiated pHEMA-collagen sponges essentially consists of the superimposition of the infrared spectrum of collagen and that of pHEMA taken separately, showing that pHEMA is present within the collagen structure (data not shown). In addition, the analysis of the amide I region shows that the interaction of pHEMA with collagen promotes an important increase of the helical content in the protein structure since the 1632 and 1660 cm$^{-1}$ features exhibit an almost equivalent intensity.

Finally, further attempts have been made in order to characterize irradiated MPEG-collagen-pHEMA sponges. As expected, the presence of three components in these samples gives rise to highly congested spectra. For this reason, conformational investigation of the secondary structure of collagen was not possible. However, it is clear both pHEMA and MPEG are present into the collagen structure.

Collagenase assay

To measure the degradability of sponges, the same collagenase assay as described above in the chemical methods was used.

In the presence of MPEG-750 or MPEG-5000, complete degradation of sponges was delayed in comparison to non-modified control sponges. The introduction of both MPEG and pHEMA broadly increased collagenase resistance or inaccessibility to collagen. PHEMA induced the most resistance to collagenase (Table 4).

Morphology of collagen sponges

The cross-sections and the surface of collagen composite materials were observed by histology and by SEM respectively. For histologic examination, specimens were either fixed with formaldehyde (3.75% in PBS). Histologic sections were routinely processed in paraffin and stained with hematoxylin phloxine saffron (HPS). Porous structures and collagen fibers morphology were qualitatively investigated by observation under light microscopy. The relative size of the porous structure was measured on histological sections using a computerized image analysis system. The surfaces occupied by the pores underlined by sponge collagen fibers were quantified. Pore areas were reported to the numbers of pores per field of observation for accurate comparison. For SEM, specimens were fixed in glutaraldehyde (2.5% in cacodylate buffer at pH7.2), then prepared as described above in the chemical methods.

Observation by SEM shows that the sponge surface was porous with a fibrillar structure that was particularly seen in the presence of both MPEG and PHEMA. Sparsely distributed deep pores were seen on the collapsed surface that was facing the air surface during the freeze drying procedure. At high magnification, well distinct and thin fibrils were observed. However, large bundles of fibers were found on the surface of sponge particularly in the presence of PHEMA with or without MPEG. The interior wall consisted of channels and pores as observed on histologic sections of specimens before implantation. Quantitative data of the relative pore surfaces showed various pattern depending on the modifications. Low molecular weight MPEG induced small pore size, except when high concentrations were used. High molecular weight MPEG induced large pore size. Combination of low molecular weight MPEG and pHEMA decreased pore size as a function of increasing concentration of MPEG. In contrast, pore size increased gradually as the concentration of high molecular weight MPEG. Relative large pore size was observed in sponges with pHEMA alone.

Cell culture studies

Using an in vitro fluid medium assay, human fibroblasts were grown until sub-confluency in 6 multiwell plates. At sub-confluency, collagen sponges were introduced in culture medium and left floating for 7 days. Cells were cultivated in the same conditions as described above in the chemical methods. During the 7 day culture period. Cells were regularly observed under phase contrast microscopy. At 7 days of culture, collagen materials and medium were removed and cells were fixed and stained with a crystal violet solution. Cell shape and cell-cell interactions were observed under microscopy.

Human fibroblasts were also seeded onto collagen materials in a form of films (0.125% collagen w/v) that were treated in a similar manner than that described above by immersion in polymers (PHEMA and/or MPEGs) and by exposition to gamma irradiation. Cells were grown up to 7 days and then observed morphologically using rhodamine-phalloidin (Molecular Probes, Eugene, Oreg.), a specific dye for F-actin. The latter procedure facilitated the indirect observation of the shape of cells laid onto collagen films.

Fluid medium assay did not show detectable cytotoxicity during the cell culture period. The cells have a normal morphology of fibroblast-like cells. They were spread and elongated onto the surface and they formed a confluent pattern similar to that observed in control wells. F-actin was regularly distributed within cells. There were no difference between the different experimental conditions in the presence of MPEGs and/or pHEMA as well as between modified collagen and non-treated collagen.

Subcutaneous implantations

Subcutaneous implantations of collagen materials were performed in mice as above described in the chemical methods.

MPEG-collagen sponges

Figure 4A:
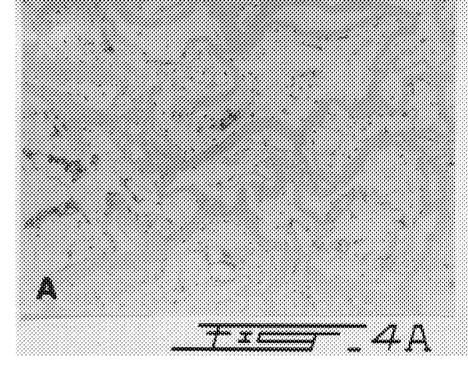
Figure 4B:
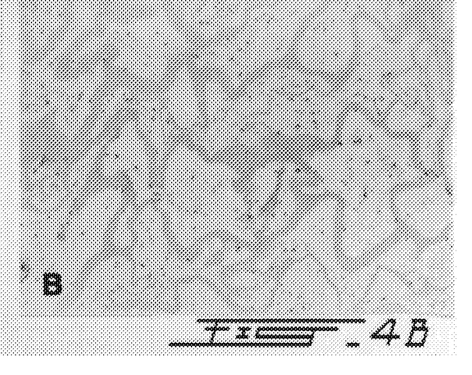

By day 7, cell infiltration by fibroblasts was limited with no obvious inflammatory reaction. By 15 days, fibroblast infiltration was observed within the porous structure (FIGS. 4A and B). The infiltration consisted of a granulation tissue with adipocytes particularly in the presence of MPEG-750. There was a very limited inflammatory reaction by days 15 and 30. By day 30, the cell infiltration occurs at a relatively similar degree than that at day 15. No fibrotic capsule was observed at any time of observation. There was no difference in tissue infiltration according to the initial concentration of MPEG introduced into collagen sponges.

HEMA-collagen sponges

Figure 4C:
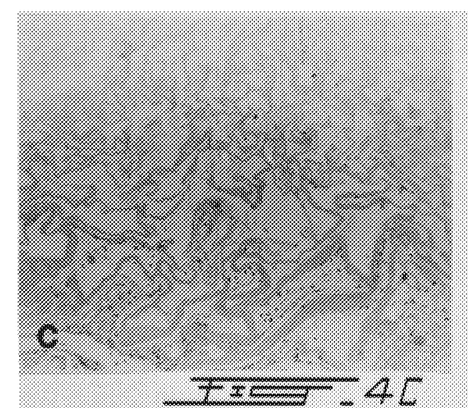
Figure 4D:
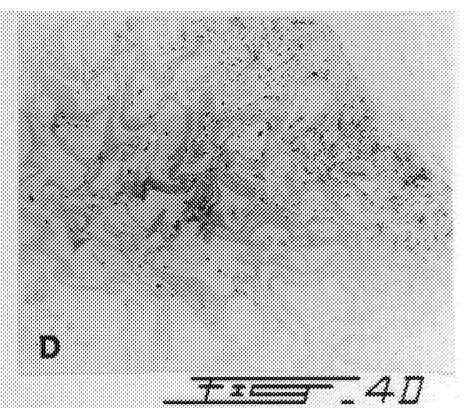
Figure 4E:
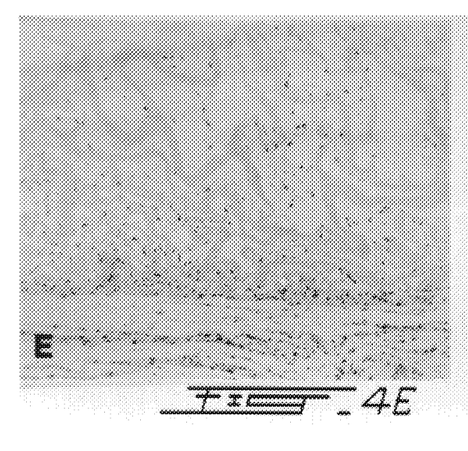

At days 7, 15, and 30, cell infiltration was limited to the surface layers of sponges. Inflammatory reaction was not observed. By day 15 and 30, a young granulation tissue was sparsely observed through the peripheral area of sponge (FIG. 4E).

MPEG-collagen-pHEMA sponges

By day 7, cell infiltration was limited to the pores situated within the superfice of sponges. No inflammatory reaction was observed. By day 15, infiltration by fibroblasts was sparsely distributed through the whole porous wall structure. Adipocytes can be observed among fibroblast-like cells, particularly in the presence of MPEG-750 (FIGS. 4C and D). However, in the presence of MPEG-750, ingrowth of a young granulation tissue was observed in the interior of the sponge while in the presence of MPEG-5000 only sparsely distributed cells can be observed. By day 30, cell or tissue infiltration was similar to that at day 15. Sparsely distributed cells were seen particularly with MPEG-5000.

Irradiated control collagen sponges

Figure 4F:
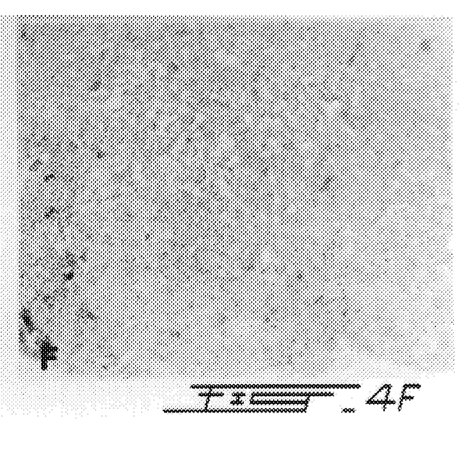

At day 7, cell infiltration was limited in the superficial pores of the sponges. However, by days 15 and 30, a gel-like mass was macroscopically found at sacrifice and the sponge structure had collapsed as observed by histology (FIG. 4F). On HPS stained tissue section, the usual yellowish stain of collagen by saffron changed to a purple stain that can be likened to denaturated collagen. A few sparsely distributed cells were observed within this collapsed structure. In addition, inflammatory reaction was moderately observed in the periphery of the sponges.

DISCUSSION

The newly prepared composite materials described hereinabove have been characterized by both physicochemical and biological methods. Biodegradable biomaterials such as collagen-based materials used as connective tissue replacement should be porous to facilitate the organization of tissue ingrowth. Such an intimate relationship between the replacement material and the organism would be beneficial: (i) for the control of in vivo biodegradation; and (ii) to organize the deposition of tissue ingrowth. In addition, the biodegradation rate of such materials should be controlled to insure an optimal duration of the artificial scaffold allowing a proper tissue reconstruction.

Our results show that MPEG-750 and -5000 activated by cyanuric chloride can be conjugated to collagen sponges and that they modify collagen behaviour. Alternatively, MPEGs or MPEG-PHEMA complex can be grafted or coated on collagen sponges during irradiation and also modify collagen behaviour. In addition, the infrared data presented therein unambiguously show that PEGs or PEG-PHEMA are present into the modified collagen sponges. These results thus indicate that PEG or PEG-PHEMA are conjugated to collagen since the water-soluble polymer is still present even after an extensive washing of the sponges. However, the efficiency of the chemical reactions might be limited by the three-dimensional structure and the compactness of collagen fibers of the sponge. This may produce a physical barrier difficult to bypass by activated PEGs, despite the use of vacuum during the conjugation process. The procedure using cyanuryl activated PEGs certainly gives a "gradient" of conjugation of PEG decreasing from the outside of the sponge to the inside. Indeed, the PEG/collagen ratios into the sponges do not only depend on the PEG concentrations in the initial solution as proved by infrared data. Therefore, the results seem to indicate that the final PEG/collagen ratio observed in the sponges is governed by complex mechanisms most likely related to the three-dimensional structure of collagen. In addition, the amount of bound PEG in PEG-conjugated enzymes can decrease the bioactivity of proteolytic enzymes, but for the same absolute mass of PEG, low molecular weight PEG is less efficacious than the high molecular weight[33]. In our study, the bioactivity of collagen may remain with PEG-750 conjugated sponges in which cell infiltration is pronounced in comparison to PEG-5000.

Using pepsinized soluble collagen, Rhee et al.[14,15] have used the formation of succinimidyl PEG glutarate to stabilize collagen. These implanted materials induce a moderate colonization by host connective tissue with a moderate inflammatory reaction and no immune response. Nevertheless, the purpose of their study[14] was limited to soluble collagen utilized for intradermal injection. It has now been discovered that PEG conjugated to collagen could also stabilize the porous structure of collagen sponge and induce tissue ingrowth as shown in the present study in which activated PEGs was introduced on a freeze-dried collagen dispersion and not within the dispersion as previously considered[15].

The toxicity and the high reactivity related to cyanuric chloride have been recently pointed out[41,42]. Our study indicates that cells and tissues are not altered by the presence of activated PEGs. Care in the purification process of PEG-cyanuryl chloride has been taken in consideration by extensive washes. Indirectly, the non-cytotoxicity activity in vitro and the non-inflammatory reaction in vivo are probably good arguments toward a very low toxicity of the conjugates. Furthermore, protein conjugates such as adenosine deaminase[43] using PEG-cyanuryl chloride have already been used with great success in humans. Nevertheless, this potentially toxic activated PEG might well be substituted by using less potentially toxic PEG activators such as:

"cyanogen bromide" (BrCN),

"amino acid esters"[47]

Derivatives of "hydrazine"[48,49,50]

Derivatives of "succinimidyl carbonate"[51]

Derivatives of "oxycarbonylimidazole"[52]

Derivatives of "nitrophenyl carbonate"[53]

Derivatives of "tresylate"[54]

Derivatives of "maleimide"[55].

It has been shown that under specific conditions (FIGS. 2 and 4), PEG could stabilize the porous structure inside collagen sponges. The latter phenomenon facilitates cell infiltration and tissue ingrowth. Our modified collagen sponges have demonstrated a significant increased resistance to collagenase targeting. In contrast to the non-modified sponges, PEG-modified sponges did not collapse up to 30 days after implantation. This event may be related to PEGs or to PEG-pHEMA complex that improve resistance towards enzymatic modifications leading to an extended biological half-life as observed with PEG-modified liposomes used as drug carriers[40,43]. The same observations have been made with enzymes such as the PEG-modified bovine adenine deaminase (PEGADEMASE™) administered to humans[44]. The PEG-modified enzyme is non-immunogenic, conserves its catalytic properties (with the proper PEG/protein ratio) and its biological half-life is significantly increased[34,36]. Thus, the stability of the PEG-modified collagen sponges might be linked to the repulsive properties of PEGs after which their covalent binding to the amino groups of the proteins stabilize the tertiary structure thereof[33]. In addition, with PEG-conjugated liposomes used as drug carriers, the repulsive barrier properties of lipid-conjugated PEG polymer chains and polymer steric stabilization are the basis for their extended in vivo circulation times.

Using the radiation method, gravimetrical measurements showed that the grafting degree of MPEG onto collagen is relatively low, averaging 5%. This implies that the MPEG macromers have low reactivity towards collagen. However, it is sufficient to induce significant changes of sponge porosity. The size of pores increased with the raise of MPEG molecular weight. This suggests that as the ether chain increases in length, there is an increased probability that the collagen fibrils become more separated by the coil of the MPEG group. Others[27] have also reported that only 4.7% radiation-grafted PEG silica gel column made the latter highly porous.

After implantation, the pore sizes of the investigated composite sponges remain stable for at least 30 days. The variations in pore sizes as observed before implantation appear were also retrieved after implantation(data not shown). This changes may be due to the effect of milieu. Furthermore, the resulting porous structure induces tissue ingrowth particularly with MPEGs.

The degree of swelling in water which is inversely proportional to density of crosslinks and/or physical entanglement of MPEG chains is much lower for all irradiation-modified sponges than for non-grafted ones. In addition, the presence of MPEG and pHEMA obviously delays or impairs collagenase activity onto collagen materials. The infrared data shows that MPEG as well as PHEMA were still present after an extensive wash of irradiated MPEG collagen and MPEG-collagen-pHEMA sponges as well as of cyanuryl-activated PEG conjugated collagen sponges.

With regard to the radiation method, these results suggest that both molecular weight MPEG and pHEMA interact with collagen upon irradiation. Strong interactions involving hydrogen bonding or electrostatic interactions with collagen may occur. The nature of the link between MPEG or pHEMA and collagen is strong enough to lead to modifications of the secondary structure of collagen. A quantitative assessment of the yields of the above reactions is difficult to measure. However, on the basis of our studies, it can be hypothesized that in results of irradiation of collagen with aqueous solution MPEG, free radicals particularly collagen (coll$^{\bullet}$), metoxy-(polyethylene glycol) (MPEG$^{\bullet}$) and species of water (hydrogen atom, hydroxyl radical, and hydrated electron; H, $^{\bullet}$OH, e$^{-}$aq) are formed. The main radiolysis products of collagen associated with the direct absorption of energy and/or concerned with the radiolytical products of water (indirect effects) are (i) macroradicals formed by abstraction of hydrogen atom from the α-carbon in protein chain; (ii) radicals created from peptide bond scission; and (iii) phenoxyl radicals and ortho, meta, and para adducts of ˙OH with tyrosine residues[10,28]. Mutual reactions between these different transients are involved in the formation of intra- and intermolecular crosslinking (structure stabilizing effect). Further, using electronic spin resonance (ESR) technique, we proved that water induces a threefold increase in the radiation yield of collagen radicals increasing markedly the extent of crosslinking[28]. Recently, Li et al[12] have also observed that the presence of water during irradiation enhances the stability of collagen matrix. The mechanism of water to protect the structure of collagen by high energy radiation is not well established. However, it is known that water molecules from hydrogen bonds between the α-chains play a significant role in stabilizing the collagen. The increase in the α-helix structure of collagen as determined by Fourier deconvolution can suggest more stable chains within collagen molecules. In addition, the presence of MPEG also enhances the biostable properties of collagen sponges. It is very probable that M˙ macroradicals formed by H atom abstracted from α-carbon position in the ether chain by $^{108}$OH radicals are involved in stabilizing processes. These macroradicals as shown previously[29] react with $O_2$ forming peroxide radicals (MPEGO$_2$˙). The latter can abstract H atoms from their own chain and/or from collagen macromolecule to give coll˙ and/or hydroxyperoxides (MPEGOOH). Peptide radicals are just reproduced and the chain reaction of collagen crosslinking may occur. The thermally instable hydroxyperoxides can easily decompose resulting in chain scissions. These fragments of oxymacro-radical (MPEGO˙) chain may combine with collagen macroradicals leading to stable structure.

Crosslinking and stabilizing processes occurring during irradiation of collagen matrix with MPEG and pHEMA combination are more complex. The grafting level and chemical composition of the materials seem to be dependent on the rate constants of a few concurrent reactions. The latter results have been recently confirmed by the establishment of the reaction kinetics (data not shown). Similar phenomena were observed by others[39] during radiation grafting of HEMA and polyethylene glycol methacrylate onto silastic film.

On a biological point of view, the polymer-collagen composites are biocompatible. The moderate inflammation as observed by 30 days with non-modified and irradiated collagen materials might be due to the early biodegradation of denaturated collagen as observed by the colour of saffron-stained collagen. In contrast, in the presence of MPEG and/or pHEMA, inflammatory reaction is not observed and the colour of collagen remained like that of normal collagen during the 30 day period of observation.

After subcutaneous implantation, MPEG-conjugated to collagen allows tissue ingrowth while the introduction of pHEMA relatively reduces cell infiltration. pHEMA has been already shown as unfavourable substrate for cell adhesion except in the presence of collagen[26]. The introduction of hydrophilic monomers such as PEGs and PHEMA with collagen enhance its hydrophilicity[22]. However, there are not the only parameters, the role of hydroxyl groups have also to be considered in cell adhesion as well as the hydrophobic/hydrophilic balance of the implant surface[41]. These surface properties may also be present within superficial and deep pore surfaces of the sponge interior. The facilitation in cell adhesion results subsequently to cell migration and cell proliferation as well, if the conditions are optimal like those in the presence of PEG-750. In addition, the infiltration of adipose tissues was also observed by others after PEG-collagen subcutaneous implantations.

Furthermore, by using the radiation methods, infection of collagen materials after subcutaneous implantation and in cell culture was not observed. The 25 kGy radiation dose as utilized seems efficient to sterilize collagen-based materials. Using this dose the probability of finding a surviving germ in the samples may be $10^6$ or less. Previously, we have shown that upon high bioburden of animal skin e.g. initial contamination at $10^8$, the dose at 25 kGy allowed to reduce microbial population to $10^{-4}$. Recently, Li et al[12] established that, for collagen matrices, sterilizing doses were usually from 16.5 kGy to 18.6 kGy. This level of irradiation has been validated to produce a sterility assurance level of $10^{-6}$ for the matrices. Radiation method not only is sufficient to equate the sterility of collagen biomaterials to that attained by other methods of sterilization but, in contrast to heat, radiation denaturation of collagen does not occur.

The developed temporary biostable scaffolds, particularly with those modified by MPEGs, could support tissue ingrowth during the wound healing process without any modification of the three-dimensional porous structure. One major problem with biodegradable implants is the optimal period that the scaffold implants remained intact within the body to allow efficacious tissue ingrowth into the scaffold. The latter could result in an organized connective tissue. Furthermore, using sterilization doses of irradiation, it is possible to offer both a biodegradable implant with stable structure and a well-suited implant for surgery in a sterile and ready-to-use state. Additional advance in this manner is that the collagen structure can be stabilized without catalysts and chemical initiators.

The process of preparing collagen and of preparing the composite collagen porous material have been conceived to maximize the amount of insoluble collagen and to avoid denaturation of the same. The latter process comprises the steps of:

a) dispersing collagen in water;

b) freezing the dispersion at about −10° to about −20° C.;

freeze-drying the dispersion at a pressure reduced under 100 millitors and about −30° to about 0° C.;

d) obtaining a collagen porous material channels of an average pore size of from about 50 μm to about 250 μm;

e) cross-linking the collagen by impregnating the same with a polyethylene molecule as defined in claim 2 at room temperature;

f) rinsing the cross-linked collagen porous material; and g) freeze-drying or air-drying the cross-linked collagen porous material to obtain a composite collagen sponge or film, respectively.

CONCLUSION

The above Examples show that more than one way can be used to produce a biostable porous wound scaffold. These examples indeed support the general teachings that the conjugation of PEG to a porous biomaterial stabilizes the size of the pores for a time necessary to encourage the ingrowth of fibroblasts, after which the conjugated biomaterial may be resorbed.

The present invention has been described hereinabove and it will be readily appreciated that obvious variations and substitutions can be made to the methods and products obtained in the practice, without departing from the spirit of this invention. These obvious variations are therefore under the scope of the present invention.

TABLE 1

In vitro collagenase assay. The times correspond to the periods for complete degradation of the collagen sponges. For PEG-modified collagen sponges, the initial concentrations of activated PEG were 1, 5 or 10 mg of collagen (w/w).

| Collagen sponges | Time (min) |
|---|---|
|  | Mean ± standard deviation |
| Non-modified | 51.6 ± 7.6 |
| PEG-750 |  |
| 1:1 | 87.5 ± 17.6 |
| 5:1 | 86.6 ± 10.4 |
| 10:1 | 90.0 ± 15.0 |
| PEG-5000 |  |
| 1:1 | 115.0 ± 8.6 |
| 5:1 | 80.0 ± 20.0 |
| 10:1 | 83.3 ± 11.5 |

TABLE 2

Grafting yield* of collagen sponge radiation modified by monomethoxy (polyethylene glycol) [MPEG], dose = 2.5 kGy.

|  | Concentration of MPEG in solution [%] | Amount of MPEG in sponge mg/100 mg collagen | Yield of grafting [%] |
|---|---|---|---|
|  | 0.30 | 5.50 | 2.4 |
|  | 0.78 | 10.13 | 4.7 |
| MPEG-750 | 1.50 | 20.97 | 6.6 |
|  | 2.98 | 46.96 | 3.3 |
|  | 4.66 | 74.00 | 5.8 |
|  | 6.03 | 90.32 | 4.2 |
|  | 0.26 | 5.30 | 1.5 |
|  | 0.79 | 14.84 | 9.0 |
| MPEG-5000 | 1.50 | 30.42 | 6.4 |
|  | 3.04 | 48.18 | 4.4 |
|  | 4.87 | 105.53 | 5.2 |
|  | 5.94 | 117.55 | 9.0 |

*Results are mean values from three measurements

TABLE 3

Absorption of monomethoxy (polyethylene glycol) (MPEG) solution in collagen sponge before irradiation and swelling of grafted sponge*, dose = 25 kGy.

|  | Concentration of MPEG in solution [%] | Solution [%] in sponge before irradiation | Swelling of grafted sponge in water [%] |
|---|---|---|---|
|  | 0.30 | 1575 | 1015 |
|  | 0.78 | 1299 | 1006 |
| MPEG-750 | 1.50 | 1398 | 908 |
|  | 2.98 | 1576 | 925 |
|  | 4.66 | 1588 | 944 |
|  | 6.03 | 1498 | 891 |
|  | 0.26 | 2050 | 1017 |
|  | 0.79 | 1879 | 965 |
| MPEG-5000 | 1.50 | 2008 | 912 |
|  | 3.04 | 1585 | 725 |
|  | 4.87 | 2167 | 762 |
|  | 5.94 | 1979 | 724 |

Swelling in water of irradiated at dose 25 kGy non-grafted sponge = 2050%
*Results are mean values from three measurements

TABLE 4

Collagenase sensitivity of grafted collagen sponges dose irradiation at 22 kGy

| Collagen sponges | Content of chemical in the sponges before irradiation [mg/100 collagen] | | TIME |
|---|---|---|---|
|  | MPEG | HEMA |  |
|  |  |  | [mn] |
| Non-modified | — | — | 45 |
| MPEG-750 | 7.0 | — | 80 |
|  | 15.6 | — | 80 |
|  | 30.0 | — | 80 |
|  | 57.6 | — | 90 |
|  | 93.2 | — | 120 |
|  | 120.6 | — | 90 |
| MPEG-5000 | 5.2 | — | 80 |
|  | 15.8 | — | 90 |
|  | 30.0 | — | 90 |
|  | 60.4 | — | 90 |
|  | 97.4 | — | 90 |
|  | 119.0 | — | 120 |
|  |  |  | [hr] |
| MPEG-750 + HEMA | 6.0 | 30 | <24* |
|  | 30.0 | 30 | <24 |
|  | 60.0 | 30 | <24 |
|  | 90.0 | 30 | <24 |
| MPEG-5000 + HEMA | 6.0 | 30 | <24* |
|  | 30.6 | 30 | <24 |
|  | 59.8 | 30 | <24 |
| HEMA | — | 20 | <48* |
|  | — | 40 | <48 |
|  | — | 60 | <48 |

*With residue

REFERENCES

1. C. J. Doillon, *Clinical Materials,* 9:189–193 (1993).
2. S. L. Schor, *J. Cell Sci.,* 41:159–175, (1980).
3. H. K. Kleinman et al. *Analyt. Biochem.,* 166:1–13 (1987).
4. P. B. van Wachem, M. J. A. van Luyn, L. H. H. Olde Damink, P. J. Dijkstra, J. Feijen, and P. Nieuwenhuis, *J. Biomed. Mater. Res.* 28:353–363 (1994).
5. E. A. Woodroof, *J. Bioeng.* 2:1–9 (1978).
6. M. F. Côte, and C. J. Doillon, *Biomaterials* 13:612–616 (1992).
7. R. Tu, R. C. Quijano, C. L. Lu, S. Shen, E. Wang, C. Hata, and D. Lin, *The International Journal of Artificial Organs* 16:537–544 (1993).
8. I. V. Yannas, and A. V. Tobolsky, *Nature* 215:509–510 (1967).
9. K. Pietrucha, *Polymers in Medicine* 19:3–18 (1989).
10. K. Pietrucha, and M. Lubis, Radiat. *Phys. Chem.* 36:155–160 (1990).
11. K. Pietrucha, Biomaterials 12:320–323 (1991).
12. P. C. Li, and S. T. Li, 20th Annual Meeting of the Society for Biomaterials, Boston, Mass., USA, Apr. 5–9 1994.
13. T. Hino, and S. Okamura, *Biocompatibility of tissue analogs* 2:72–87 (1985).
14. W. Rhee, J. Carlino, S. Chu, and H. Higley, in *Biotechnical and biomedical applications*, J. M. Harris (ed.), Plenum Press, New York, 1992, pp. 183–198.
15. W. Rhee, D. G. Wallace, A. S. Michaels, R. A. Burns, L. Fries, F. DeLustro and H. Bentz, U.S. Pat. No. , 5,162,430 (1992).
16. A. Morawiecki, and S. Song, EP Patent 568334 A (1994).
17. J. Freidenreich, U. Schick, J. Werry, and J. Wunderlich, WO Patent 9313753 A (1994).

18. M. Chvapil, R. Holusa, K. Kliment, et al, *J. Biomed. Mater. Res.* 3:315–332 (1969).
19. M. Stol, I. Cifkova, V. Tyrackova, and M. Adam, *Biomaterials* 12:454–460 (1991).
20. J. K. Rao, D. V. Ramesh and K. P. Rao, *Biomaterials* 15:383–389 (1994).
21. S. Amudeswari, B. Nagarajan, C. Rami Reddy and K. Thomas Joseph, *J. Biomed. Mater. Res.* 20:1103–1109 (1986).
22. L. Civerchia-Perez, B. Faris, G. LaPointe, J. Beldekas, H. Leibowitz, and C. Franzblau, *Proc. Natl. Acad. Sci.* 77:2064–2068 (1980).
23. H. P. Corkhill, C. J. Hamilton, and B. J. Tighe, *Biomaterials* 10:3–10 (1989).
24. Tokyo Contact Lens, JP Patent 62071924 (1994).
25. M. Carenza, *Radiat. Phys. Chem.* 39:485–493 (1992).
26. M. F. Côte, E. Sirois, and C. D. Doillon, *J. Biomater. Sci. Polymer Ed.* 3:301–313 (1992).
27. L. G. Garkevenko, A. V. Kiselev, Y. S. Nikitin, and J. N. Topchieva, *Kolloidn. Lh.* 48:534–536 (1986).
28. K. Pietrucha, W. Pekala, and A. Plonka, *Radiat. Phys. Chem.* 16:315–318 (1980).
29. J. Marchal, *Radiat. Res.,* 327–338 (1967).
30. Y. H. Sun, W. R. Gombotz, and A. S. Hoffman, *J. Bioact. Compat. Polym.* 1:316–334 (1986).
31. M. J. Lydon, T. W. Minett, and B. J. Tighe, *Biomaterials* 6:396–402 (1985).
32. D. P. Speer, M. Chvapil, C. D. Eskelson and J. Ultreich, *J. Biomed. Mat. Res.* 14:753 (1980).
33. C. Delgado, G. E. Francis and D. Fisher, *Rev. Ther. Drug Carrier Syst.* 9:249 (1992).
34. A. Abuchowski, J. R. McCoy, N. C. Palczuk, T. van Es and F. F. Davis, *J. Biol. Chem.* 252:3578 (1977).
35. H. C. Chiu, S. Zalipsky, P. Kopeckova and J. Kopecek, *Bioconjug Chem.* 4:290 (1993).
36. M. S. Hershfield, R. H. Buckley, M. L. Greenberg, A. L. Melton, R. Schiff, C. Hatem, J. Kurtzberg, M. L. Markert, R. H. Kobayashi, A. L. Kobayashi and A. Abuchowski, *New Eng. J. Med.* 316:589 (1987).
37. A. Apicella, B. Cappello, M. A. Del Nobile, M. I. La Rotonda, G. Mensitieri and L. Nicolais, *Biomaterials* 14:83 (1993).
38. A. Nathan, S. Zalipsky, S. I. Ertel, S. N. Agathos, M. L. Yarmush and J. Kohn, *Bioconjug. Chem.* 4:54 (1993).
39. I. Saiki, J. Yoneda, Y. Igarashi, M. Aoki, N. Kusunose, K. Ono, I. Azuma, *Jpn J. Cancer Res.* 84:558 (1993).
40. G. Blume, G. Cevc, M. D. Crommelin, I. A. Bakker-Woudenberg, C. Kluft and G. Storm, *Biochim. Biophvs. Acta.* 1149:180 (1993).
41. S. Zalipsky, R. Seltzer and S. Menon-Rudolph, *Biotech. Appl. Biochem.* 15:100 (1992).
42. Y. Gitoh, M. Tsukada and N. Minoura, *Bioconjugate Chem.* 4:554 (1993).
43. M. C. Woodle, K. K. Matthay, M. S. Newman, J. E. Hidayat, L. R. Collins, C. Redemann, F. J. Martin and D. Papahadjopoulos, *Biochim. Biophys. Acta* 1105:193 (1992).
44. A. A. Bogdanov, Jr., R. Weissleder, H. W. Frank, A. V. Bogdanova, N. Nossif, B. K. Schaffer, E. Tsai, M. I. Papisov and T. J. Brady, *Radiology* 187:701 (1993).
45. D. Needham, T. J. McIntosh and D. D. Lasic, *Biochim. Biophys. Acta* 1108:40 (1992).
46. E. J. Miller and R. K. Rhodes *Methods Enzymol.* 82:33–64 (1982).
47. S. Zalipsky et al., *J. Macromol. Sci. Chem.* A21:839 (1984).
48. M. Rubinstein, U.S. Pat. No. 4,101,380 (1978).
49. F. F. Davis et al, U.S. Pat. No. 4,179,337 (1979).
50. L O Persson & B. Olde, (1988) *J. Chromatog.* 457:183 (1988).
51. T. Miron et al. *Bioconjugate Chem.* 4:568 (1993).
52. T. Allen et al. *Biochem. Biophys. Acta* 1066:29 (1991).
53. L. Sartore et al. *Appl. Biochem. Biotech.* 27:45 (1991).
54. A. L. Klibanov, et al. *Biochem. Biophys. Acta* 1062:142 (1991).
55. T. P. Kogan, Synthetic Commun. 22:2417 (1992).

What is claimed is:

1. A biomaterial of a stable porosity which comprises a porous biopolymer matrix into which is impregnated and conjugated a polyethylene molecule having a substituted ether end, which is conjugated to said biopolymer through a reactive group present on said biopolymer.

2. A biomaterial as defined in claim 1 wherein said polyethylene molecule has the following formula:

$$A-O-(CH_2-CH_2-O)_m-(CH_2)_n-Z$$

wherein:

m is an integer comprised between 2 and 500;

n is an integer comprised between 1 and 7;

A is a substituent represented as a moiety prior to its linkage at its left end to said reactive group of said biopolymer, said moiety being selected from the group consisting of:

B—CR=CH—, wherein R is hydrogen or a lower alkyl, and B is hydrogen, carboxy, hydroxy, aldehyde, $NH_2$— or SH—;

cyanuric chloride or hydrogen cyanide;

$_2$OS—X—$CH_2$—, wherein X is absent or a linear, branched or aromatic group of 1 to 6 carbon atoms;

D—OOC—$(CH_2)_o$—, wherein o is an integer comprised between 1 to 7, and D is, hydrogen, an anhydride, a mixed anhydride or an activated ester of 1 to 8 carbon atoms;

—N—$(CH_2)_o$—, wherein o is an integer comprised between 1 to 7;

—S—$(CH_2)_o$, wherein o is an integer comprised between 1 to 7;

—Z is selected from the group consisting of:

hydrogen;

—FGE wherein F is $O^-$, $N^-$ or $S^-$, G is hydrogen, a lower alkyl, a cycloalkyl of 1 to 7 carbon atoms or —C(O)—I, wherein I is a reactive group of a pharmaceutical agent, and E is absent hydrogen or a lower alkyl; and —C(O)—JE, wherein J is hydrogen, a lower alkyl, a cycloalkyl of 1 to 7 carbon atoms or —O—K, wherein K is a reactive group of a pharmaceutical agent, and E is absent hydrogen or a lower alkyl.

3. A material according to claim 1 wherein said biopolymer is selected from collagen, crosslinked gelatin, fibronectin, larninin, vitronectin, fibrinogen/fibrin, glycosaminoglycans, Matrigel™ basement membrane matrix, cellulose, chitosan and chitin.

4. A material according to claim 2 wherein said biopolymer is selected from collagen, crosslinked gelatin, fibronectin, laminin, vitronectin, fibrinogen/fibrin, glycosaminoglycans, Matrigel™ cellulose, chitosan and chitin.

5. A material according to claim 3 wherein said biopolymer is collagen.

6. A material according to claim 4 wherein said biopolymer is collagen.

7. A material according to claim 5 wherein said biopolymer is type I collagen.

8. A material according to claim 6 wherein said biopolymer is type I collagen.

9. A material according to claim 2 wherein A is acrylate or methacrylate.

10. A material according to claim 3 wherein A is acrylate or methacrylate.

11. A material according to claim 6 wherein A is acrylate or methacrylate.

12. A material according to claim 9, 10 or 11, wherein said conjugation is performed by gamma radiation.

13. A material according to claim 2 wherein said pharmaceutical agent is a growth factor.

14. A material according to claim 13 wherein said growth factor is selected from the group consisting of: FGF, EGF, TGF, PDGF, TNF, IGF, CSF, NGF, heparin binding growth factor, interferons, erythropoeitin, interleukins and tissue activating peptides.

15. A material according to claim 2, 4 or 6 wherein A is cyanuric chloride, m is an integer comprised between 7 to 45, n is 1 and Z is hydrogen.

16. A material according to claim 2, 4 or 6 wherein A is $D-O(O)C-(CH_2)_{3-5}$ wherein D is hydrogen, or succinimidyl, m is an integer comprised between 7 to 45, n is 1 and Z is hydrogen.

* * * * *

UNITED STATES PATENT AND TRADEMARK OFFICE
CERTIFICATE OF CORRECTION

PATENT NO. : 5,863,984

DATED : January 26, 1999

INVENTOR(S) : Charles J. Doillon, Montchatel, Canada;

Krystina Pietrucha, Lodz, Poland;

René C. Gaudreault, Berniéres, Canada

It is certified that error appears in the above-identified patent and that said Letters Patent is hereby corrected as shown below:

At Col. 24, line 54, please delete "larninin," and insert -- laminin, --

Signed and Sealed this

Fourteenth Day of December, 1999

*Attest:*

Q. TODD DICKINSON

*Attesting Officer*  *Acting Commissioner of Patents and Trademarks*